United States Patent [19]
LeMole

[11] Patent Number: 5,893,369
[45] Date of Patent: Apr. 13, 1999

[54] PROCEDURE FOR BYPASSING AN OCCLUSION IN A BLOOD VESSEL

[76] Inventor: Gerald M. LeMole, 404 Tomlinson Rd., Huntingdon Valley, Pa. 19006

[21] Appl. No.: 08/804,598

[22] Filed: Feb. 24, 1997

[51] Int. Cl.$^6$ ................................................ A61B 17/32
[52] U.S. Cl. .......................................................... 606/184
[58] Field of Search .............................. 623/1, 2, 11, 12, 623/66; 606/184, 185, 139, 152, 153, 154; 604/164, 165, 166, 167, 168

[56] References Cited

U.S. PATENT DOCUMENTS

| | | | |
|---|---|---|---|
| 5,403,338 | 4/1995 | Milo | 606/184 |
| 5,669,918 | 9/1997 | Balazs et al. | 606/153 |
| 5,695,504 | 12/1997 | Gifford, III et al. | 606/153 |

FOREIGN PATENT DOCUMENTS

| | | | |
|---|---|---|---|
| 2028070 | 12/1971 | Germany | 606/184 |

*Primary Examiner*—David J. Isabella
*Attorney, Agent, or Firm*—Seidel, Gonda, Lavorgna & Monaco, PC

[57] ABSTRACT

A bypass procedure for connecting a bypass conduit to a blood vessel to channel a flow of blood around an occlusion. The procedure involves attaching a bypass conduit to a portion of the blood vessel at first and second locations. A collar is utilized to suture the graft to blood vessel. A punching device is inserted into one of end of the bypass conduit. The punching device preferably includes a punch and a block. The block is inserted through a cut formed in the blood vessel wall. Concomitant actuation of the block and punch toward one another severs a section of the blood vessel wall to form a channel into the bypass conduit. The present invention also discloses preferred implements for use in the bypass procedure. A cutting device can be utilized to form the cuts in the vessel wall and may be either integral with or separate from the block. In one embodiment, the block is expandable between a collapsed state and an expanded or inflated state. The block is inserted into the lumen of the blood vessel in its collapsed state. An inflating medium is injected into the handle of the block which causes that block to expand to its expanded operative state. In another embodiment, the block is pivotable about a handle to facilitate positioning within the lumen. A guide wire can be utilized in the bypass procedure to guide the implements to the blood vessel wall.

15 Claims, 16 Drawing Sheets

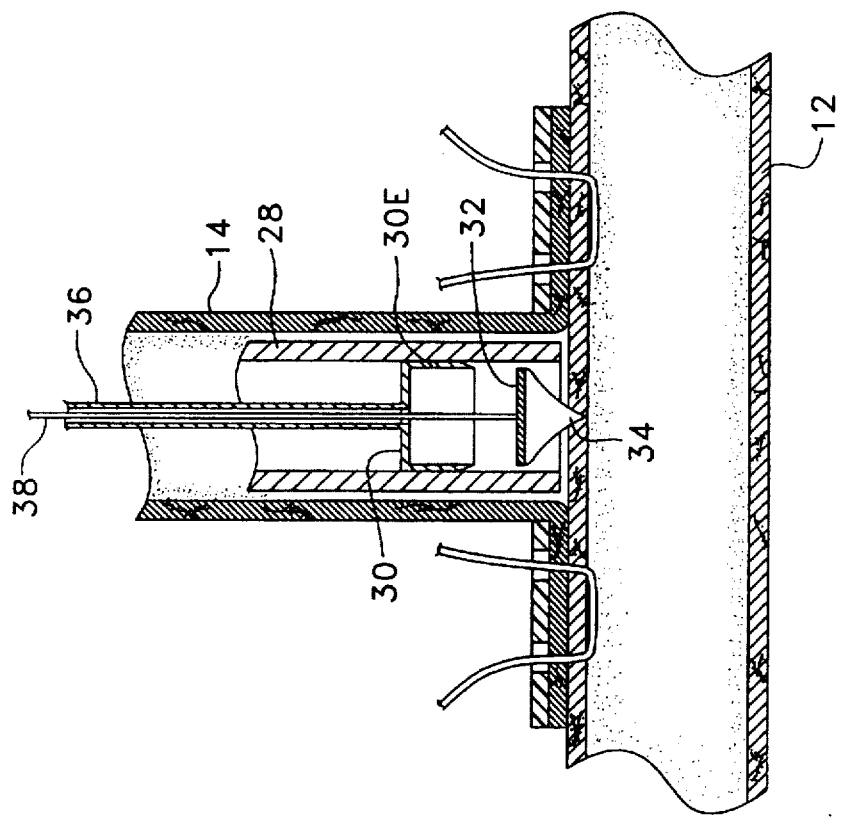
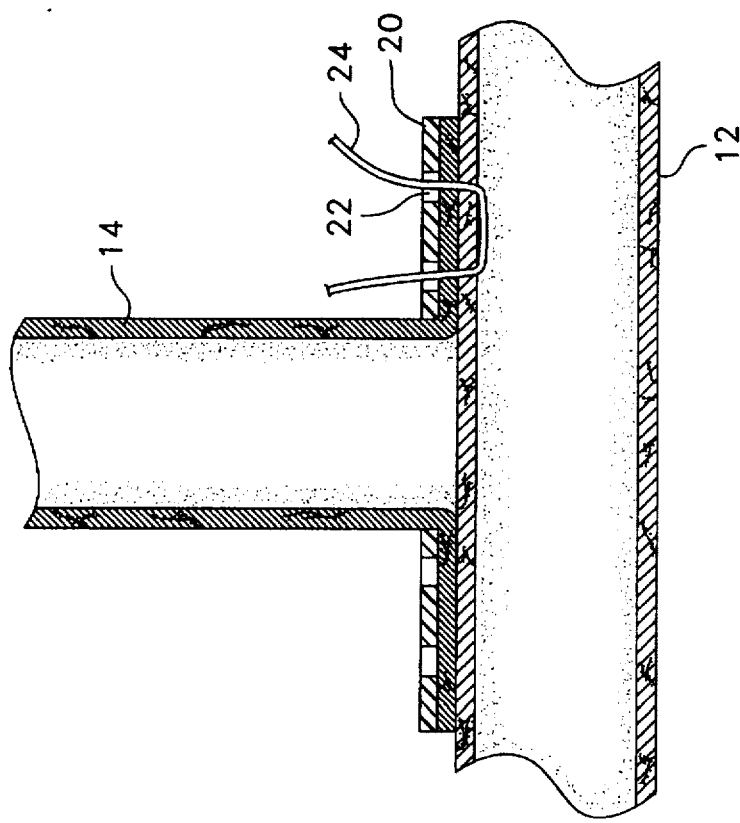

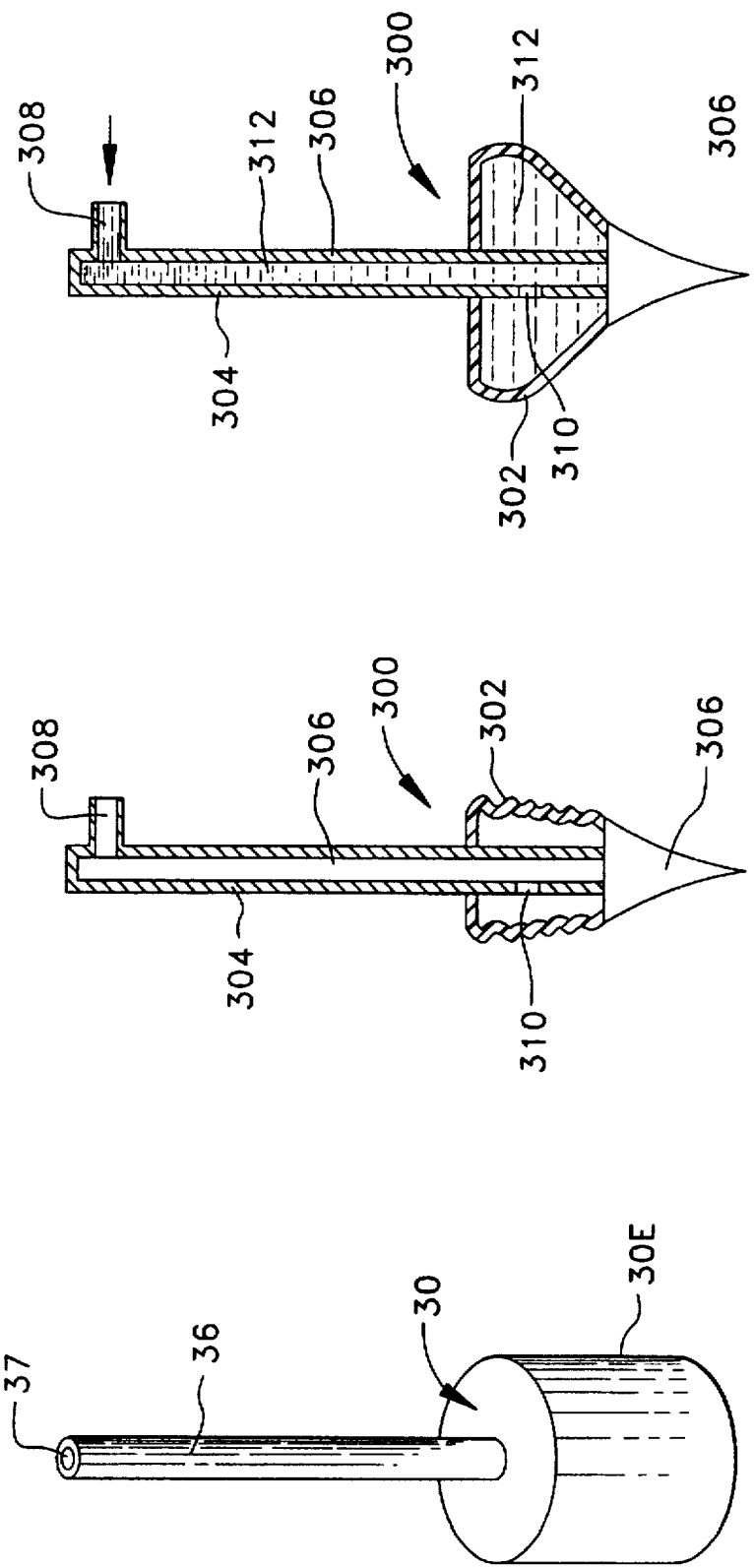

5,893,369

PROCEDURE FOR BYPASSING AN OCCLUSION IN A BLOOD VESSEL

FIELD OF THE INVENTION

The invention relates to an improved procedure for bypassing an occluded or damaged blood channel. More particularly, the present invention provides a novel bypass method, with accompanying implements, for bypassing an occluded artery or vein in a patient.

BACKGROUND OF THE INVENTION

Atherosclerosis is a disease which affects the blood vessels in a cardiovascular system. This disease involves thickening of the vessel walls caused by the accumulation of fat, fibrin, cellular debris and/or calcium. As the vessel wall thickens, the internal lumen of the vessel narrows. This is commonly referred to as stenosis. Vessel stenosis impedes and reduces blood flow through the vessel. Hypertension and disfunction can result in organs which are downstream from the vessel stenosis due to the reduced blood flow.

One complication associated with the thickening of the vessel is the loss of its ability to expand and contract. Additionally, the thickening of the vessel wall reduces the vessels viability. This results in increased likelihood that an aneurysm will develop. If the patient suffers from hypertension or elevated blood pressure, ann developing aneurysm will frequently dissect and ultimately rupture.

Small vessels, such as the arteries that supply blood to the heart, legs and intestines are particularly susceptible to atherosclerotic narrowing. The loss of blood supply to the leg or segment of the intestine may result in the development of gangrene. Atherosclerotic narrowing of the coronary arteries impedes, limits and, in some instances, prevents blood flow to regional areas of the heart. Depending upon the severity of the narrowing and its location within the coronary circulation, pain, cardiac dysfunction or death may result. Larger vessels can also develop atherosclerosis.

In cases where atherosclerotic disease is advanced and the attendant complications jeopardize the health of the patient, surgical intervention is usually instituted. If the disease is extensive and the vessel is no longer reliable, it is usually replaced or bypassed by a graft. Conventionally this procedure involves placing the patient on a heart bypass machine while the diseased portion of the vessel is transected and removed. A graft, either synthetic or biologic, is attached between the transected sections of the vessel. This grafting procedure is called anastomosis.

A biologic graft is usually a non-critical artery or vein of small diameter which is harvested from elsewhere in the body, such as the internal mammary artery. When no suitable artery or vein can be harvested, or where time prevents harvesting of a suitable biological vessel, a synthetic vessel can be used. Synthetic vessel are conduits made from biocompatible material, such as DACRON® polyester fiber (DACRON is a registered trademark of E.I. du Pont de Nemours & Co., Inc., Wilmington, Del.), or polytetrafluoride (PTFE).

As described above, conventional heart bypass surgery requires that the patient be placed on a heart-lung machine and stoppage of the blood flow along the diseased vessel. This is a very time consuming procedure. Moreover, placing a patient on an extracorporeal circuit may result in complications, such as a stroke, myocardial infarction, infection, or hemorrhage.

A need, therefore, exists for a bypass procedure which eliminates the need for placing the patient on an extracorporeal circuit. A need also exists for a bypass procedure which minimizes the likelihood of damage to the host vessel.

SUMMARY OF THE INVENTION

The present invention is directed to a bypass procedure and associated implements for connecting a bypass conduit to a blood vessel to channel a flow of blood around an occlusion. The procedure involves selecting a bypass conduit suitable for channeling the flow of blood. An artificial biocompatible graft or harvested blood vessel from the patient can be utilized if desired. The bypass conduit has first and second ends which are utilized in the attachment portion of the procedure.

The bypass conduit is attached to a portion of the blood vessel at a first location. Preferably, a collar is placed over and sutured to the graft to blood vessel attachment interface.

A punching device is inserted into one of end of the bypass conduit. The punching device preferably includes a punch and a block. The block is inserted through a cut formed in the blood vessel wall at the first location. Concomitant actuation of the block and punch toward one another severs a section of the blood vessel wall of suitable size to permit flow of blood. The punching device is then removed from the bypass conduit.

The bypass conduit is then attached to the blood vessel at a second location preferably on the opposite side of the occlusion. The attachment of the blood vessel can be by any suitable means. However, in one preferred embodiment, a cut is formed in the side of the blood conduit. A collar is then sutured between the blood conduit and the blood vessel wall.

A punching device is inserted into the terminal end of the bypass conduit. The punching device preferably includes an angled punch and a block arrangement. The block is inserted through the cut formed in the blood conduit and a cut in the blood vessel wall. Concomitant actuation of the block and punch toward one another severs a section of the blood vessel wall of suitable size to permit flow of blood. The punching device is then removed from the bypass conduit.

The terminal end of the bypass conduit is then closed either by suturing or clipping.

A sleeve can be inserted into the bypass conduit before insertion of the punching device in order to protect the walls of the bypass conduit from damage.

The cuts that are formed in the blood vessel wall can be made by a separate cutting device that is inserted into the bypass conduit. Alternately, the cutting device can be formed as an extension of the block.

The present invention contemplates forming the block several different preferred ways. In one embodiment, the block is expandable between a collapsed state and an expanded or inflated state. In this embodiment, the block is inserted into the lumen of the blood vessel in its collapsed state. An inflating medium is injected into the handle of the block which causes that block to expand to its expanded state. In its expanded state, the block forms a surface which, when actuated in combination with the punch, severs a segment of the blood vessel wall.

In another embodiment, the block is pivotable about the handle. The pivoting of the block facilitates positioning of the block within the lumen of the blood vessel. A guide wire can be utilized to guide the implements to the blood vessel wall.

The foregoing and other features and advantages of the present invention will become more apparent in light of the following detailed description of the preferred embodiments thereof, as illustrated in the accompanying figures.

BRIEF DESCRIPTION OF THE DRAWINGS

For the purpose of illustrating the invention, the drawings show a form of the invention which is presently preferred. However, it should be understood that this invention is not limited to the precise arrangements and instrumentalities shown in the drawings.

FIG. 5 is a section view of the graft after it is attached to the blood vessel in an end-to-side grafting according to the present invention.

FIG. 6 illustrates the cutting of the wall of the blood vessel using block and punch instruments designed for the use in the present invention.

FIG. 9A is a perspective view of one embodiment of the punch according to the present invention.

FIGS. 12A through 12F illustrate an alternate block embodiment according to the present invention as it is used to remove a portion of the vessel wall.

DETAILED DESCRIPTION OF THE PREFERRED EMBODIMENTS

Figure 1:
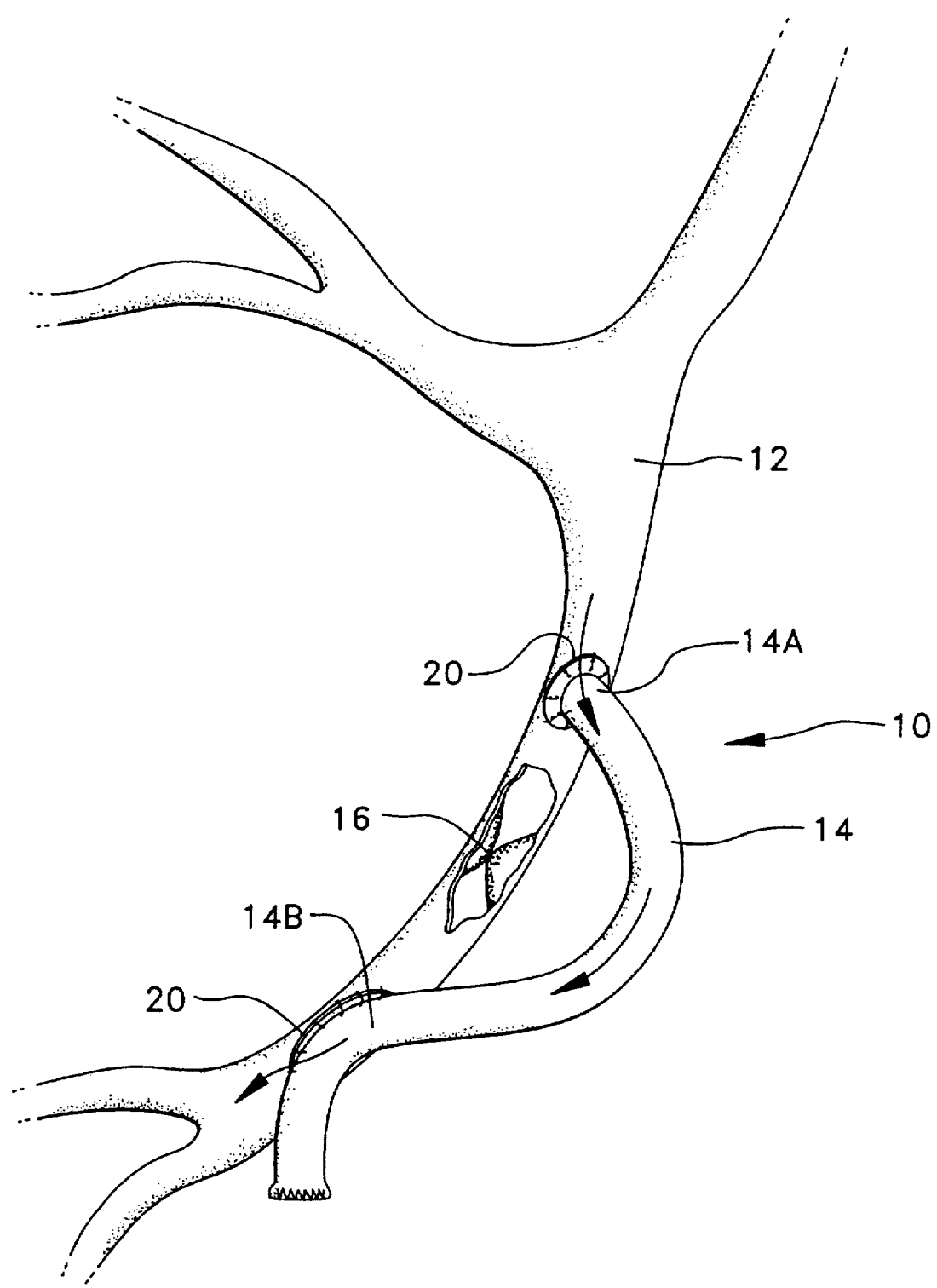
FIG. 1 illustrates an arterial bypass made according to the present invention.

Referring now to the drawings, wherein like reference numerals illustrate corresponding or similar elements throughout the several views, FIG. 1 illustrates a bypass 10 in a blood vessel 12, such as an artery or a vein, according to the present invention. The bypass utilizes a bypass conduit or graft 14 to channel blood around an occlusion, restriction, or defect 16, such as an aortic dissection, in the blood vessel 12 (the blood flow is illustrated by the arrows in the figure). The occlusion or restriction 16 is a narrowing of the blood vessel 12 caused by build-up of matter on the walls of the lumen, or by damage from an injury. For the sake of simplicity, the narrowing of the lumen, whether complete or partial, will be referred to as an occlusion. It is contemplated that the present invention can be practiced on any suitable blood carrying vessel (such as a vein, an anterior descending artery or the aorta).

As shown in FIG. 1, the graft 14 is attached upstream and downstream of the occlusion 16. As will be discussed in more detail below, the present invention contemplates attachment of the graft 14 to the host vessel 12 through either an end-to-side attachment $14_A$ or a side-to-side attachment $14_B$. The graft 14 is preferably a harvested vein or artery from the patient. More preferably, the graft is an internal mammary artery (IMA) which has been harvested from under the patient's breast plate. The length and diameter of the graft 14 is chosen to accommodate the volume of flow and location of the occluded vessel. If a major artery or vein is being bypassed, more than one graft 14 can be used to bypass the occluded portion. After harvesting, the graft is prepared in a conventional manner. Harvesting and preparing of grafts is well known to those skilled in the art and, therefore, no further discussion is required for the present invention. If harvesting the graft from the patient is not possible or desirable, a synthetic or similar type graft can be utilized in the present invention.

Figure 2:
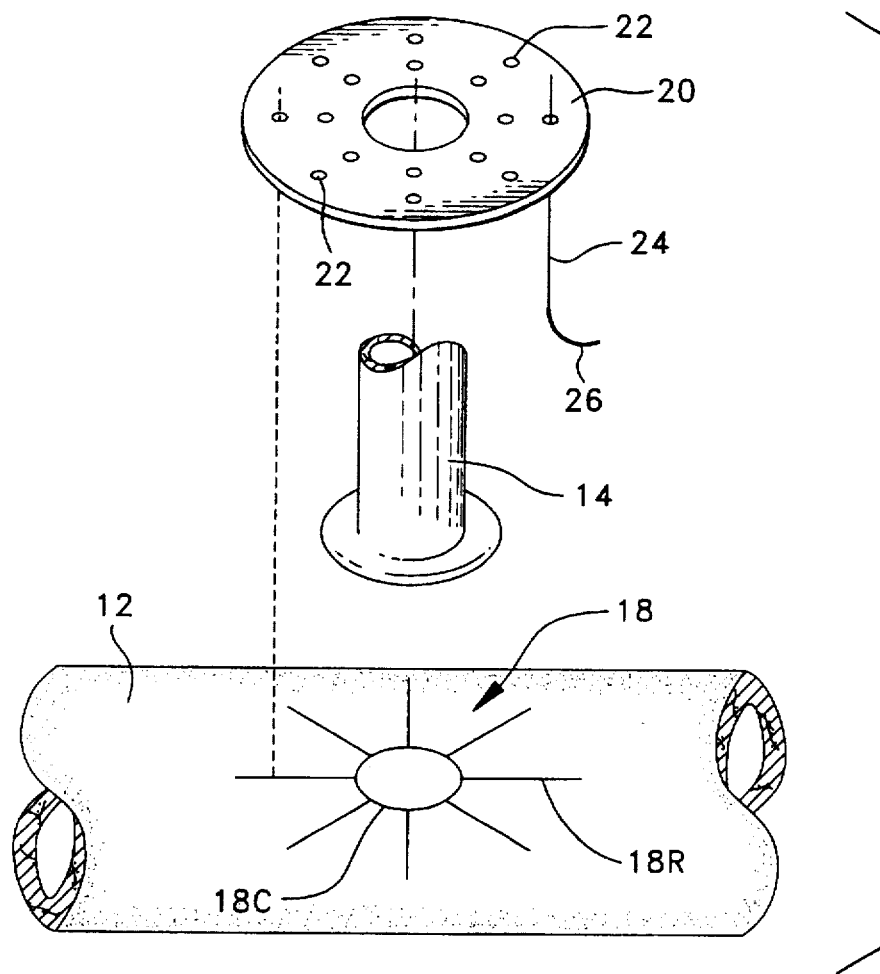
FIG. 2 illustrates an end-to-side positioning of a graft onto a blood vessel according to the present invention.
Figure 3:
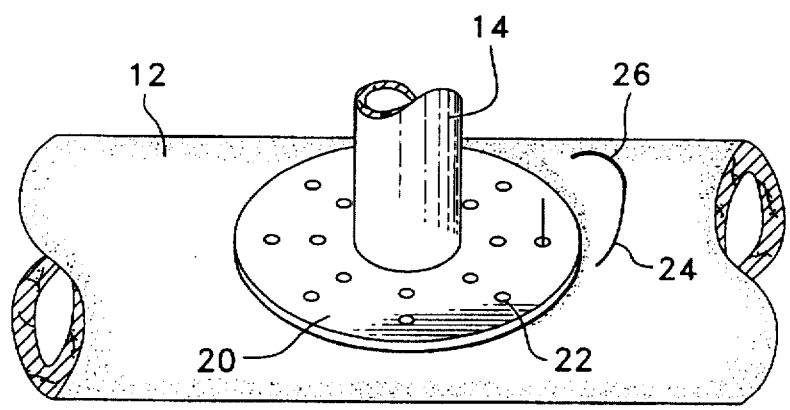
FIG. 3 illustrates an end-to-side attachment of the graft.

After acquiring the proper length of graft 14, the graft 14 is attached to the host vessel 12. In one preferred embodiment, the upstream end of the graft 14 is first attached to the host vessel 12. As illustrated in FIG. 1, the upstream attachment is preferably made via an end-to-side attachment or grafting. Referring to FIGS. 2 and 3, prior to attachment of the graft 14, the host vessel is preferably marked with a sterile marking pen upstream of the occlusion in a suitable location where the host vessel has not become hardened or calcified. FIG. 2 illustrates a marking configuration 18 which is useful in the present invention. The marking configuration 18 includes a circular pattern $18_C$ which defines the proposed diameter of the aperture which will ultimately channel the blood from the host vessel 12 through the bypass graft 14. The marking configuration 18 also has a plurality of rays $18_R$ extending radially outward from the circular pattern $18_C$. As will be discussed in more detail hereinafter, the rays $18_R$ and the circular pattern $18_C$ provide a guide for attaching the graft 14 to the host vessel 12. During a bypass procedure, the graft 14 is positioned onto the host vessel 14 such that the lumen of the graft 14 is substantially concentric with the circular pattern $18_C$.

Figure 4A:
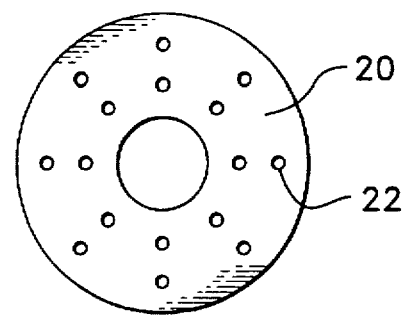
FIGS. 4A through 4C illustrate collars which are used for attaching grafts to existing blood vessels in the present invention.
Figure 4B:
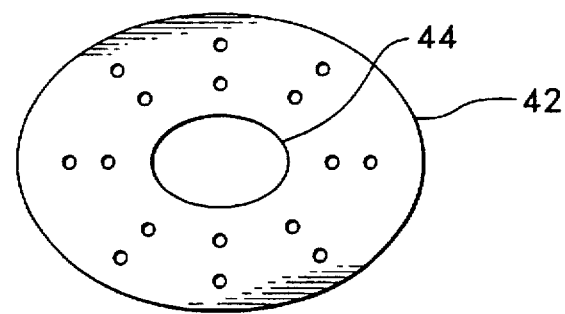
Figure 4C:
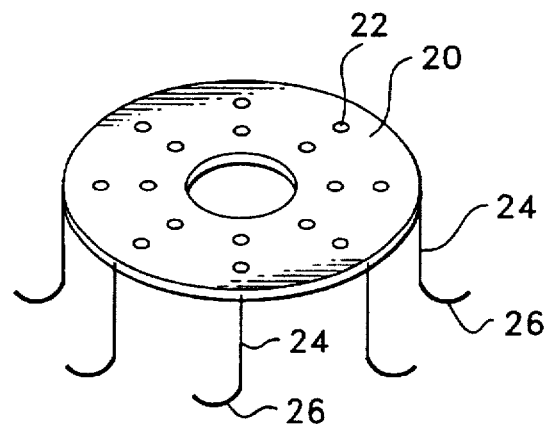

A collar 20 is used to attach the graft 14 to the host vessel 12. In a side-to-end graft attachment, the collar 20 is positioned over the end of the graft 14 so as to provide a tissue-to-tissue interface between the graft 14 and the host vessel 12. A tissue-to-tissue attachment biologically provides a more efficient seal between the graft 14 and the host vessel 12. FIG. 4A illustrates one circular collar 20 contemplated for use in this embodiment of the invention. The collar 20 has an inner diameter which is slightly larger than the outer diameter of the graft 14. In one configuration, the inner diameter of the collar 20 is between about 3½ and 5½ millimeters. The outer diameter of the collar 20 is about 5 centimeters (about 2 inches) and the thickness of the collar 20 is between about 2 and 3 millimeters. The collar 20 preferably has a plurality of holes 22 formed through it for permitting passage of sutures 24 and needles 26. The sutures 24 attach the graft 14 and vessel 12 to the collar 20. The holes 22 are arranged around the collar 20 in a prescribed pattern in order to provide a suitable attachment. In the embodiment illustrated, the holes are arranged radially in groupings of two. The arrangement of holes is intended to line up with the rays $18_R$ of the marking configuration 18 to provide guidance for suturing the graft 14 to the vessel 12. In order for the rays $18_R$ to be visible when attaching the collar 20, the rays $18_R$ extend radially outward farther than the outer diameter of the collar 20. Alternates shapes and configurations are well within the scope of the invention. For example, the sutures 24 and needles 26 could be physically attached to the collar 20, as shown in FIG. 4C. The collar 20 can be made from any material which is biologically compatible with human tissue, such as silicon, inert plastic, polypropylene or polyethylene.

It is also contemplated that instead of conventional thread and needle sutures, a needle and latch arrangement, such as the device shown in U.S. Pat. No. 3,570,497, can be used with or attached to the collar 20. U.S. Pat. No. 3,570,497 is incorporated herein by reference in its entirety. In order to prevent the leakage of blood, a sealant may be added around the collar 20. The sealant is preferably a fibrin glue sold by the Fibrin Corporation of Wilmington, Del. U.S. Pat. No. 5,420,250 describes in detail the preparation of a preferred fibrin glue and is incorporated herein by reference in its entirety. FIG. 5 is a cross-sectional illustration of the graft 14 and host vessel 12 after attachment of the collar 20. As shown, the inner diameter of the graft 14 provides a bypass conduit for the blood to flow along.

Referring to FIG. 6, after the graft 14 is attached to host vessel 12, a sleeve 28 is preferably inserted into the graft 14. The sleeve 28 serves to prevent any implements which are subsequently placed into the graft 14 from damaging the inside surface of the graft wall. Furthermore, if the graft 14 is not an internal mammary artery but, instead, is a vein, the sleeve 28 also assists in opening up valves (not shown) which line the sides of the graft wall. The valves are arranged so as to permit flow in one direction and restrict flow in the opposite direction. Hence, it is important to attach the graft to the host vessel such that the flow along the bypass is unrestricted. (Alternately, the valves could be removed prior to attachment of the graft to the host vessel.) It is also contemplated that the sleeve 28 could be inserted into either end of the graft 14 prior to attachment to the host vessel 12. This permits the lumen of the graft 14 to be maintained in an open state while the collar 20 is attached to the graft 14 and the vessel 12. Moreover, if the upstream end of the graft 14 is attached first (as shown in FIG. 1), the sleeve 28 must be inserted prior to attachment since, by necessity, the valves will prevent insertion of the sleeve 28 after attachment.

The size of the sleeve will vary depending on the diameter of the graft lumen and the desired diameter for the bypass hole that will be formed in the wall of the host vessel 12. Preferably the outer diameter of the sleeve 28 is slightly smaller than the graft lumen diameter within the collar 20. The sleeve is preferably made from thin walled plastic material, such as tetrafluoroethylene resin (sold under the name TEFLON®), or polypropylene. TEFLON is a registered trademark of E.I. du Pont de Nemours & Co., Inc., Wilmington, Del. With the sleeve 28 positioned inside the graft 14, the physician has direct access to the outer wall of the host vessel 12.

Figure 10:
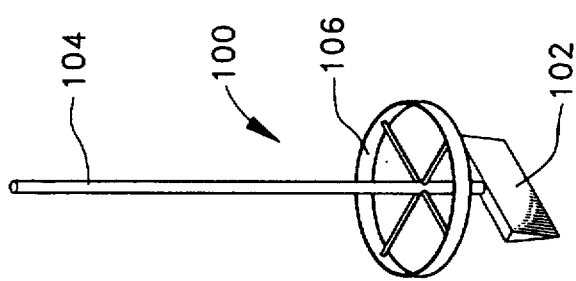
FIG. 10 is a perspective view of one embodiment of the cutter according to the present invention.

The next step of the procedure involves piercing or cutting the wall of the host vessel 12. In order to achieve this, the physician inserts a cutter or knife (shown in FIG. 10) into the sleeve 28. The cutter is generally designated by the numeral 100. The 100 cutter includes a cutting edge 102 which is attached to a cutter handle 104. The cutter handle 104 can be flexible or rigid so long as it provides the physician with sufficient control to cut the wall of the host vessel. As shown, the cutter 100 preferably includes a spacer ring 106 mounted to a portion of the cutter handle 104. The spacer ring 106 is sized to fit within the internal diameter of the sleeve 28. The spacer ring 106 maintains the cutting edge 102 in spaced relationship from the walls of the sleeve 28 thereby preventing any inadvertent damage. The spacer ring 106 can be made from any suitable material, such as plastic.

Figure 8:
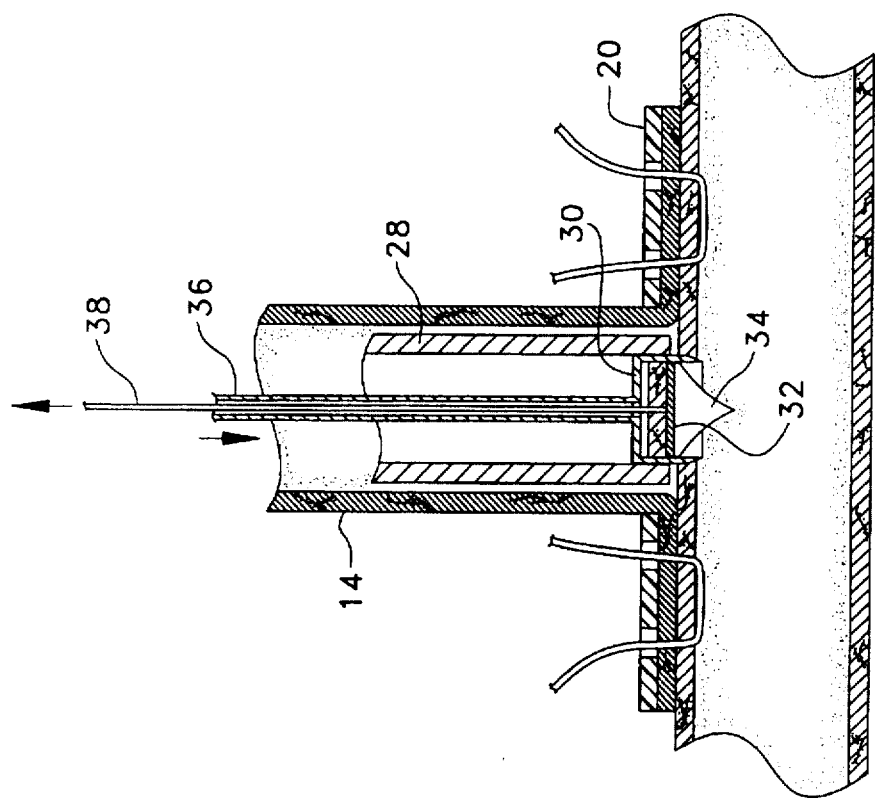
FIG. 8 illustrates the wall of the blood vessel immediately after a hole is punched through it.
Figure 7:
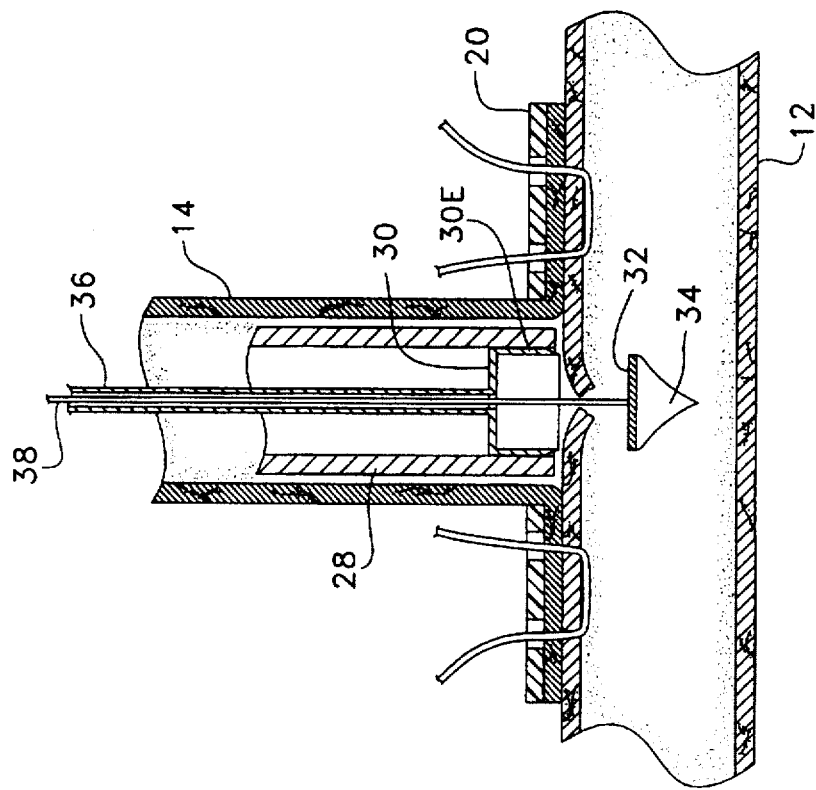
FIG. 7 illustrates the wall of the blood vessel immediately after piercing with the block.
Figure 9C:
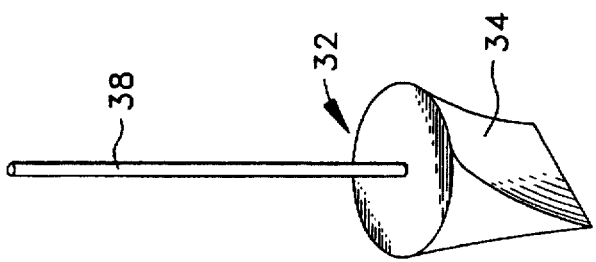
FIG. 9C is a perspective view of another embodiment of the block according to the present invention.
Figure 9B:
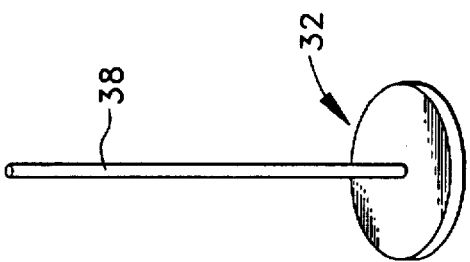
FIG. 9B is a perspective view of one embodiment of the block according to the present invention.

A device for removing a portion of the vessel wall is then inserted into the sleeve 28. Preferably, the removal device comprises a punch 30 and block (or die) 32 arrangement as shown in FIG. 6. The punch 30 has a peripheral cutting edge $30_E$ that, acting in conjunction with the block 32, cuts an opening through vessel wall which will define the inlet for the blood into the bypass. FIGS. 7 and 8 illustrate the punch 30 and block 32 in use. FIG. 9A is a perspective view of the punch 30 and FIG. 9B is a perspective view of the block 32. The block 32 is inserted through the cut in the vessel wall and into the lumen of the vessel 12. The punch 30 is then positioned against the exterior surface of the vessel wall. The punch 30 is translated toward the vessel wall (shown by the downward arrow in FIG. 8) while, concomitantly, the block 32 is translated toward the punch 30 (shown by the upward arrow in FIG. 8). As a consequence, the vessel wall between the punch 30 and block 32 is sheared off and captured within the punch 30. The capturing of the sheared vessel wall segment within the punch 30 prevents the tissue from entering into the blood stream and causing subsequent damage.

Preferably the punch 30 and block 32 are designed to slidingly fit within the sleeve 28 and configured to remove a circular shaped portion of the vessel wall. As shown in FIGS. 6 and 9C, the block 32 may also be formed with a sharp cutting edge 34 depending from its lower surface to pierce the wall of the vessel 12. The sharp cutting edge 34 eliminates the need for a separate cutter 100 as described in the previous step. The cutting edge 34 preferably tapers outward as it extends upward to the lower surface of the block 32. This shape facilitates insertion of the block 32 into the interior of the vessel 12. The punch 30 includes a depending punch side wall $30_W$ which terminates in a sharp edge. The depending punch wall $30_W$, apart from its use in cutting the host vessel wall, also acts to guide the punch 30 along the sleeve 28 so that the punch wall $30_W$ engages the vessel wall at approximately a ninety (90) degree angle.

To further guarantee accurate actuation of the punch 30 and block 32, the punch 30 has a hollow punch handle 36 extending upward through the sleeve 28 in the opposite direction from the punch wall $30_W$. The punch handle 36 is of sufficient length to extend out of the opposite end of the graft 14 and permit grasping by a physician or other medical personnel.

The block 32 has a block handle 38 that extends upward from the top of the block 32 and within the hollow 37 of the punch handle 36. The block handle 38 has a length which is longer than the length of the punch handle 36 thereby permitting the punch handle 36 to be held with one hand and the block handle 38 with the other hand.

The punch and block handles 36, 38 are preferably positioned substantially in the center of the punch 30 and block 32, respectively, and can be attached by any suitable means (e.g., fixed, pivotal). Handgrips (not shown) may be incorporated at the distal ends of the handles to facilitate actuation. Alternately, the distal ends of the punch and block handles 36, 38 may be attached to an actuation mechanism (not shown) which permits single handed actuation of the punch 30 and block 32.

If the cross-sectional shapes of the punch 30 and block 32 are not circular, then it may be desirable to form the punch and block handles 36, 38 with a non-circular cross-section so as to ensure accurate interaction between the punch 30 and block 32. For example, the punch handle 36 can be formed with a square hollow cross-section. The block handle 38 can be formed with a square cross-section that slides within the hollow cross-section of the punch handle 36. Accordingly, the handles will be constrained to move only axially with respect to one another. The punch 30 and block 32 can be made from any suitable material, such as stainless steel or plastic. The diameters of the punch 30 and block 32 will vary depending on the graft lumen and sleeve diameters and the desired bypass inlet size. It is also possible to limit the separation of the block 32 and the punch 30 so that the block 32 is prevented from passing too far into the host vessel 12.

Figure 11A:
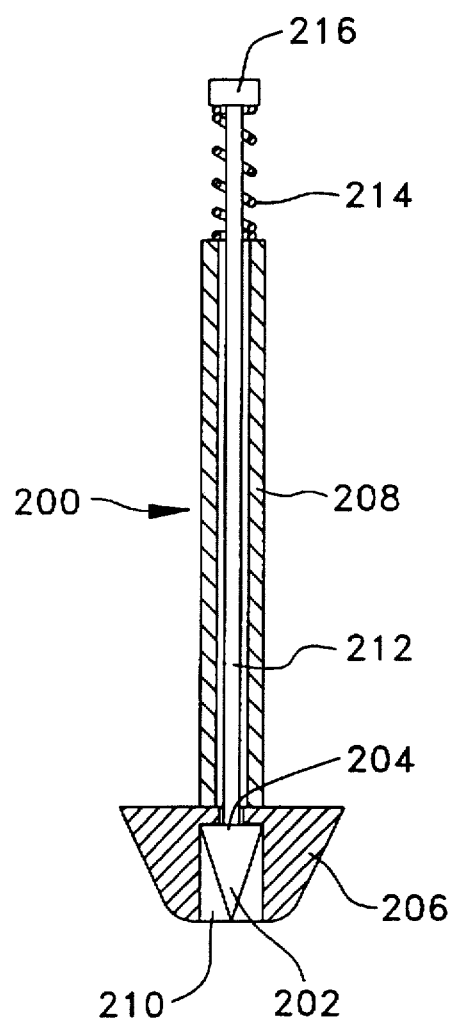
FIG. 11A and 11B are cross-sectional views of an alternate embodiment of the combined cutter and block according to the present invention.
Figure 11B:
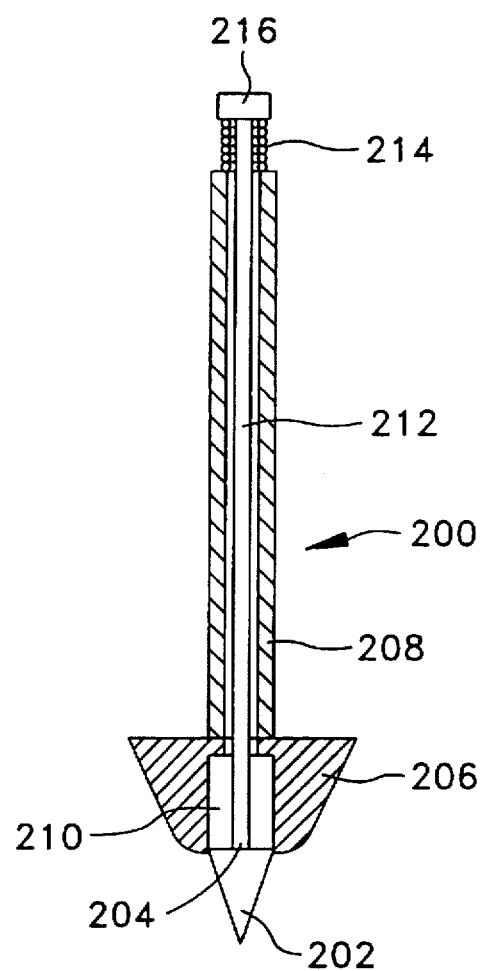

Various other embodiments for the punch 30 and block 32 are within the scope of this invention. For example, the cutting edge 34 can be retractable so as to prevent inadvertent puncturing of the host vessel wall opposite the opening being formed. This embodiment of the invention is shown in FIGS. 11A and 11B, and is generally designated by the numeral 200. As shown, a cutting edge 202 of a cutter 204 is retractable within a portion of a block 206 and/or block handle 208. The block 206 has a recessed cavity 210 formed in its bottom surface. The recessed cavity 210 is sized to accept a cutting edge 202. The cutting edge 202 is attached to a cutter handle 212 which extends within a hollow interior of the block handle 208. Preferably a spring or similar reciprocating means 214 is mounted at the top between the block handle 208 and the cutter handle 212. An actuator knob or depression device 216 is mounted to the top of the cutter handle 212 which extends past the top of the block handle 208. The spring 214 biases the knob 216 axially away from the top of the block handle 208. This causes the cutting edge 202 to seat within the recess 210 in the block 206 when the actuator knob 216 is not depressed. In use, the physician inserts the block 206 and cutter 204 combination into the sleeve 28 and against the host vessel wall. The physician then depresses the knob 216 causing the cutting edge 202 to extend out from the block 206 as shown in FIG. 11B. This causes the cutting edge 202 to sever the host vessel wall. The physician next removes pressure from the knob 216 causing the cutting edge 202 to retract back into the recess 210 in the block 206. The physician then urges the block 206 through the severed cut in the vessel wall and into the lumen of the host vessel 12. Since the cutting edge 202 is retained within the recess 210 in the block 206 (or alternately within the handle), there is minimal likelihood of damage to the opposite wall of the host vessel.

Figure 12A:
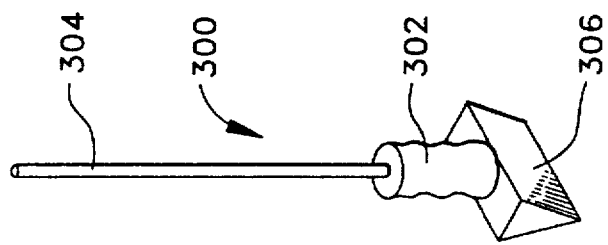
Figure 12D:
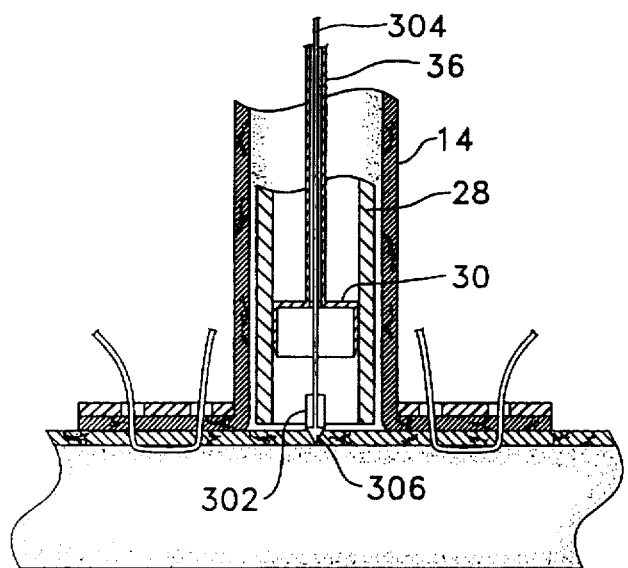
Figure 12E:
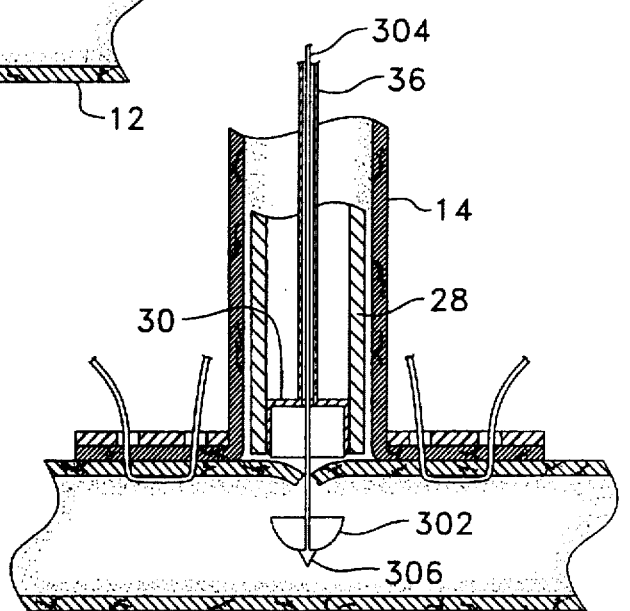
Figure 12F:
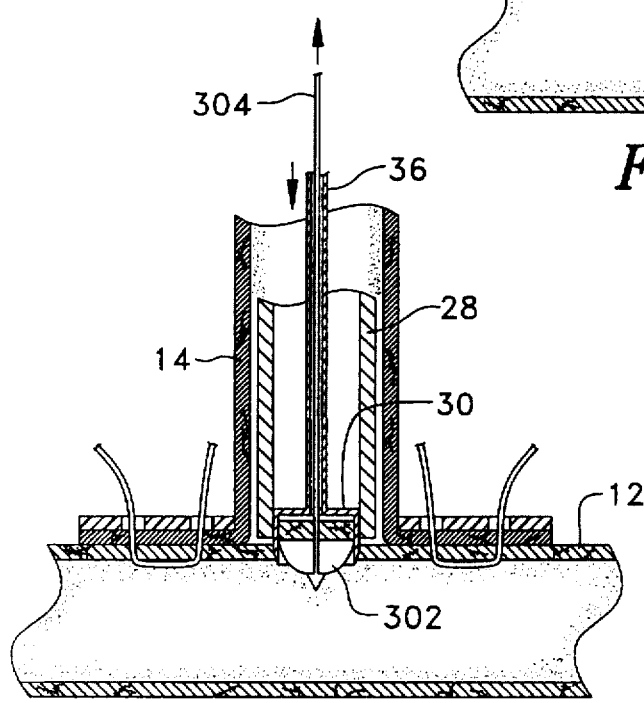

FIGS. 12A through 12F illustrate another embodiment of the block as contemplated by the present invention, and is generally designated with the numeral 300. In this embodiment, the block 302 is designed to be inflatable or expandable from a retracted or collapsed position to a punching position. FIG. 12A illustrates in perspective view the expandable block 302. As shown in FIGS. 12A, 12B and 12D, the block 302 in its initial position is collapsed around a block handle 304. The block 302 preferably includes a cutting edge 306 located at its lower end for piercing the vessel wall when in use. Both the cutting edge 306 and the retracted block 302 are shown positioned within the host vessel 12 in FIG. 12E. An inflating medium, such as an isotonic saline solution, is injected into the block 302. One method of injecting the inflating medium into block 302 is by including a channel 306 within the block handle 304 that acts as a conduit from the top of the handle 304 to the block 302. Referring to FIGS. 12B and 12C, the channel 306 extends from an upper portion of the block handle 304 down into the inflatable block 302. The channel 306 communicates with an upper inlet port 308 which is designed to permit injection of an inflating medium into a block handle 304. A lower exit port 310 is shown extending between the interior of the block 302 and the channel 306. FIG. 12C illustrates the channel 306 and block 302 filled with an inflated medium 312 after it is injected into the upper inlet port 308. The inflating medium 312 causes the block to expand laterally outward. A syringe or similar implement can be used to inject the inflating medium into the handle 304. Approximately about 0.05 to about 0.5 cc's of inflating medium would be sufficient to inflate the block 302. The block 302 is preferably made from a strong plastic material, such as a polyester film sold under the trade name MYLAR®. MYLAR is a registered trademark of E.I. Du Pont de Nemours & Co., Inc., Wilmington, Del. Referring to FIG. 12F, after inflation, the punch 30 and block 302 are actuated in a similar manner as discussed above. The severed portion of the vessel wall will be trapped between the inflated block 302 and the punch 30 as it is removed from the sleeve 28. The diameter of the inflated block 302 should be less than the inside diameter of the sleeve 28 so as to allow the inflated block 302 to be removed after punching the vessel wall. Those skilled in the art can readily appreciate that many other variations can be practiced within the scope of the invention.

An additional benefit of utilizing any of the punch and block embodiments described above in practicing the present invention is that, after the vessel wall has been sheared off, the punch and block prevent the blood from flowing along graft 14. Hence, as the punch and block are being removed, the graft 14 can be clamped with a soft occluding clamp, such as a "bull dog" clamp, in the vicinity of the attachment to host vessel 12. This allows the distal end of th graft 14 to be attached to the host vessel 12 downstream from the occlusion without loss of blood.

Figure 13:
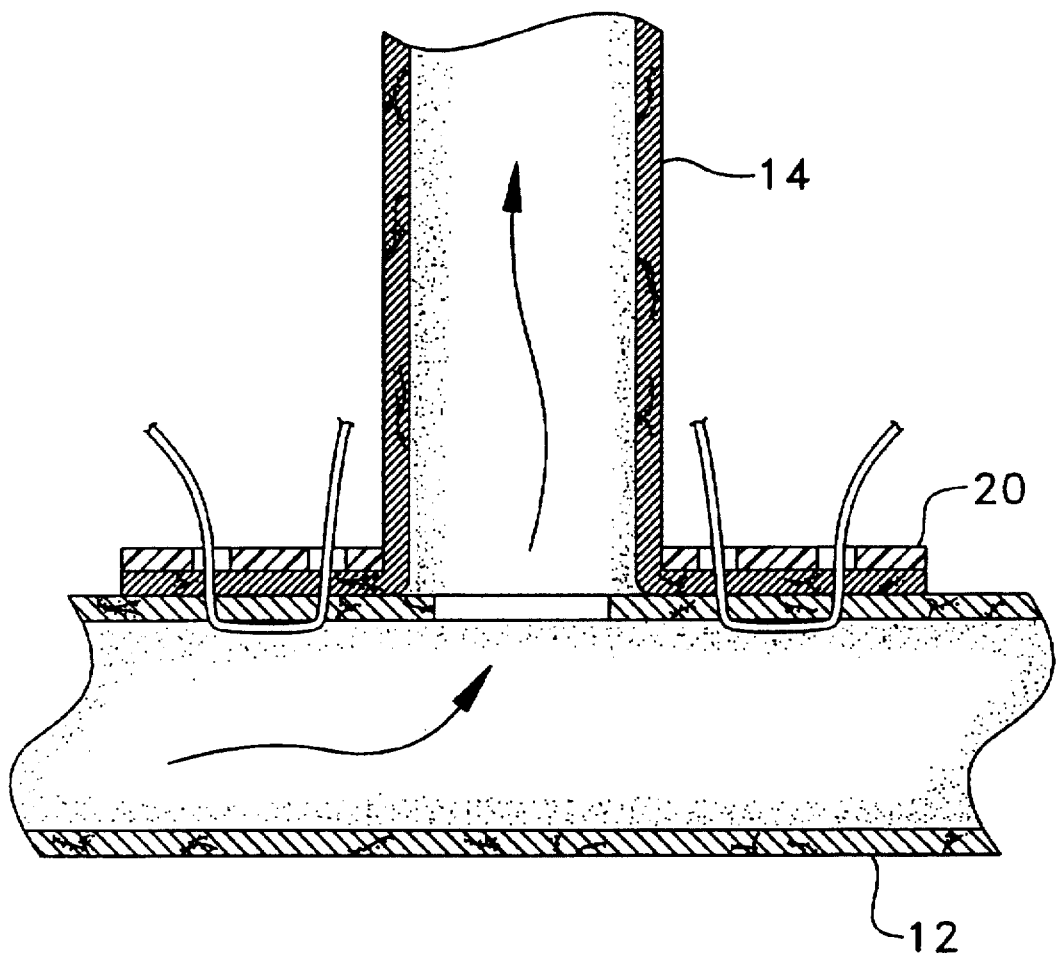
FIG. 13 illustrates the completed attachment of the graft to the side wall of the blood vessel.

FIG. 13 illustrates a completed end-to-side bypass grafting. Blood can freely flow from the host vessel 12 through the opening and into the graft 14 as illustrated by the arrows.

Figure 14:
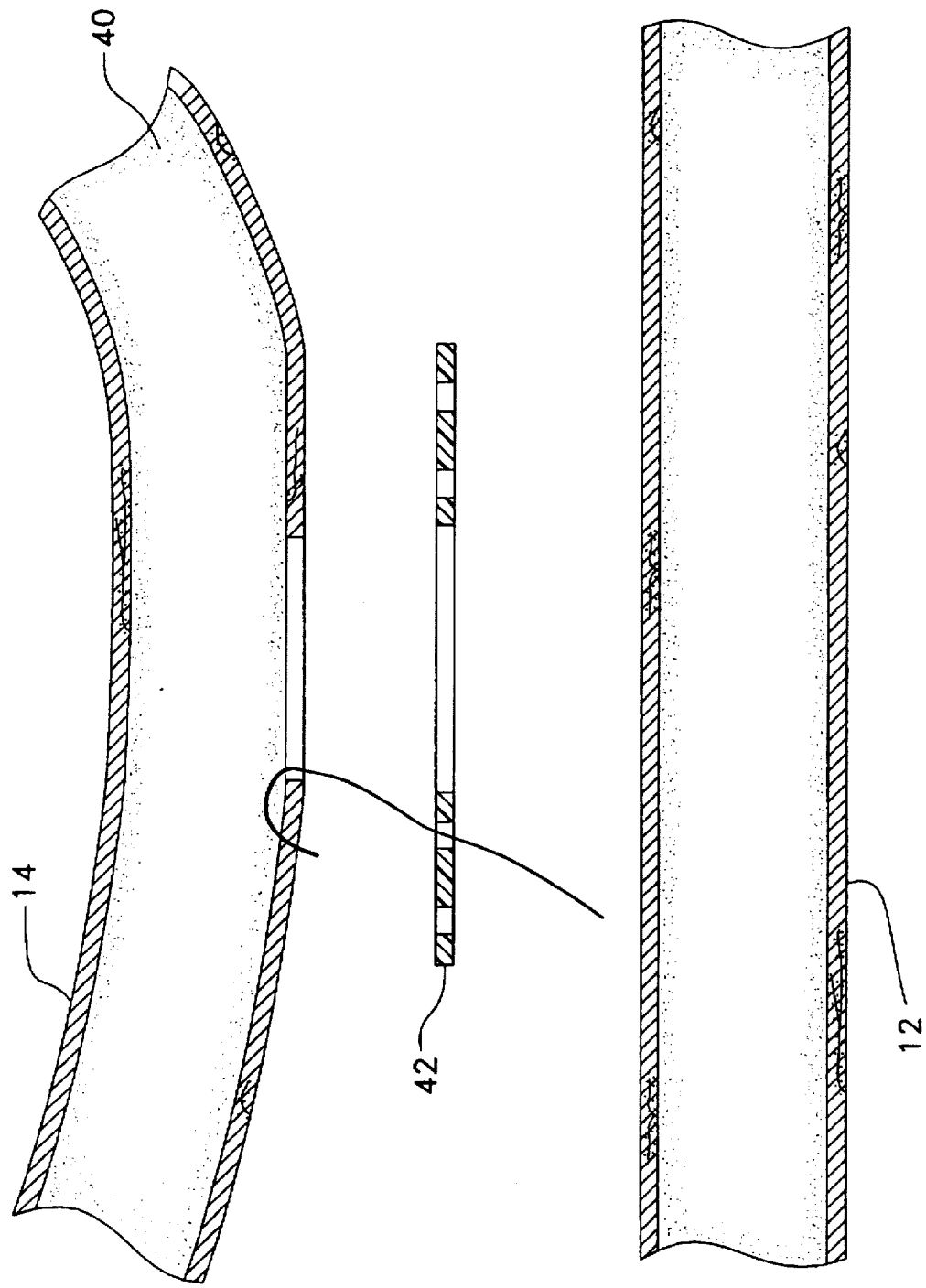
FIG. 14 illustrates a side-to-side attachment of a graft onto a blood vessel according to the present invention.

The above procedure is one preferred method of performing an end-to-side attachment of a graft 14. This method, however, is not a preferred method for attaching the second end of the graft 14 since it is difficult to form a hole in the vessel wall through the graft 14 without placing the patient on a heart-lung machine. However, a modified version of the above procedure can be used without the need for a heart-lung machine. In this alternate embodiment, a side-to-side mating of the graft 14 and host vessel 12 is used. Referring to FIG. 14, one preferred side-to-side arrangement is shown for mounting the graft 14 to the host vessel 12. A terminal end of the graft 14 is identified by the numeral 40. A portion of the graft 14 adjacent to the terminal end 40 is placed against the host vessel 12 downstream from the occlusion as shown in FIG. 1. As will be discussed in more detail below, an aperture will be made between the graft 14 and the host vessel through the terminal end 40.

A opening is made in the graft 14 at a suitable location. A second collar 42, similar to the first collar 20, is placed between the graft 14 and the host vessel 12. The second collar 42 preferably has an elliptical inside opening 44 as shown in FIG. 4B. As will be discussed in more detail below, the elliptical opening 44 is configured to permit insertion and removal of implements at an angle to the vessel wall. The design of the second collar 42 is otherwise the same as the first collar 20. The collar 42 is sutured to the graft 14 and host vessel 12 as shown.

Figure 15:
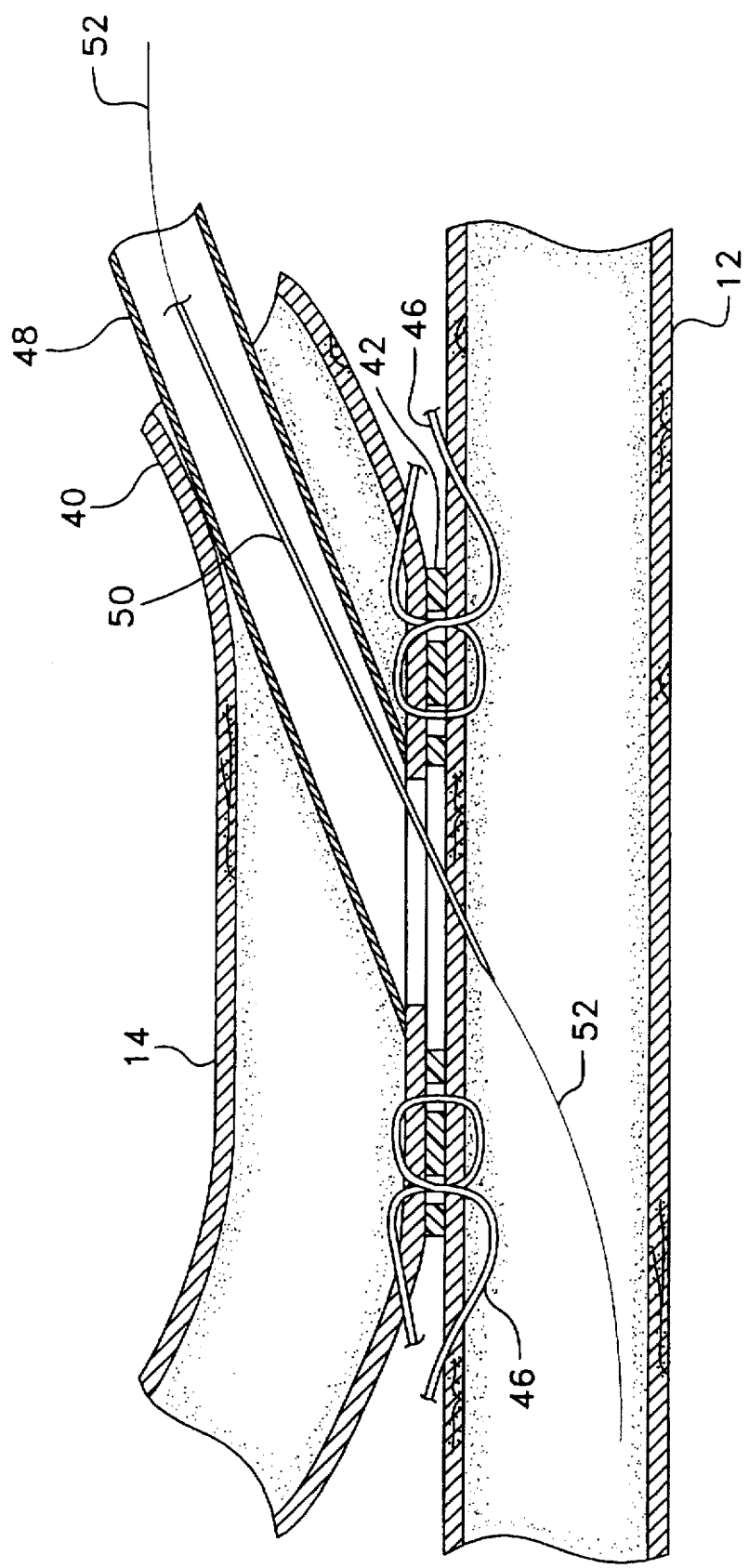
FIG. 15 illustrates insertion of a guide wire in a side-to-side attachment of a graft according to the present invention.

Referring now to FIG. 15, the graft 14 is shown attached to the host vessel 12 through a series of sutures 46. As with the previous embodiment, alternate methods of attachment are also contemplated by the present invention and are well within the purview of the claims. An angled sleeve 48 is inserted into the terminal end 40 of the graft 14. The angled sleeve 48 is similar to the sleeve 28 used in the end-to-side attachment described above, i.e., a thinned walled plastic tube for guiding medical implements during the grafting procedure. The bottom of the angled sleeve 48 preferably sits substantially flush with the interior of the graft wall.

A needle 50 is inserted into the angled sleeve 48 and through both the graft wall and the host vessel wall. The needle 50 is preferably made from a rigid material, such as stainless steel or aluminum, that will sustain the forces required to puncture the vessel and graft walls. The needle 50 has a channel formed through it. After insertion of the needle through the graft and vessel walls, a guide wire 52 is passed through the channel and into the lumen of the host vessel 12 such that a portion of the guide wire 52 is within the lumen of the host vessel 12 and a portion extends out of the terminal end 40 of the graft 12. The needle 50 is then removed leaving the guide wire 52. The guide wire 52 acts as a means for directing or guiding medical instruments to the graft and vessel walls.

Figure 16:
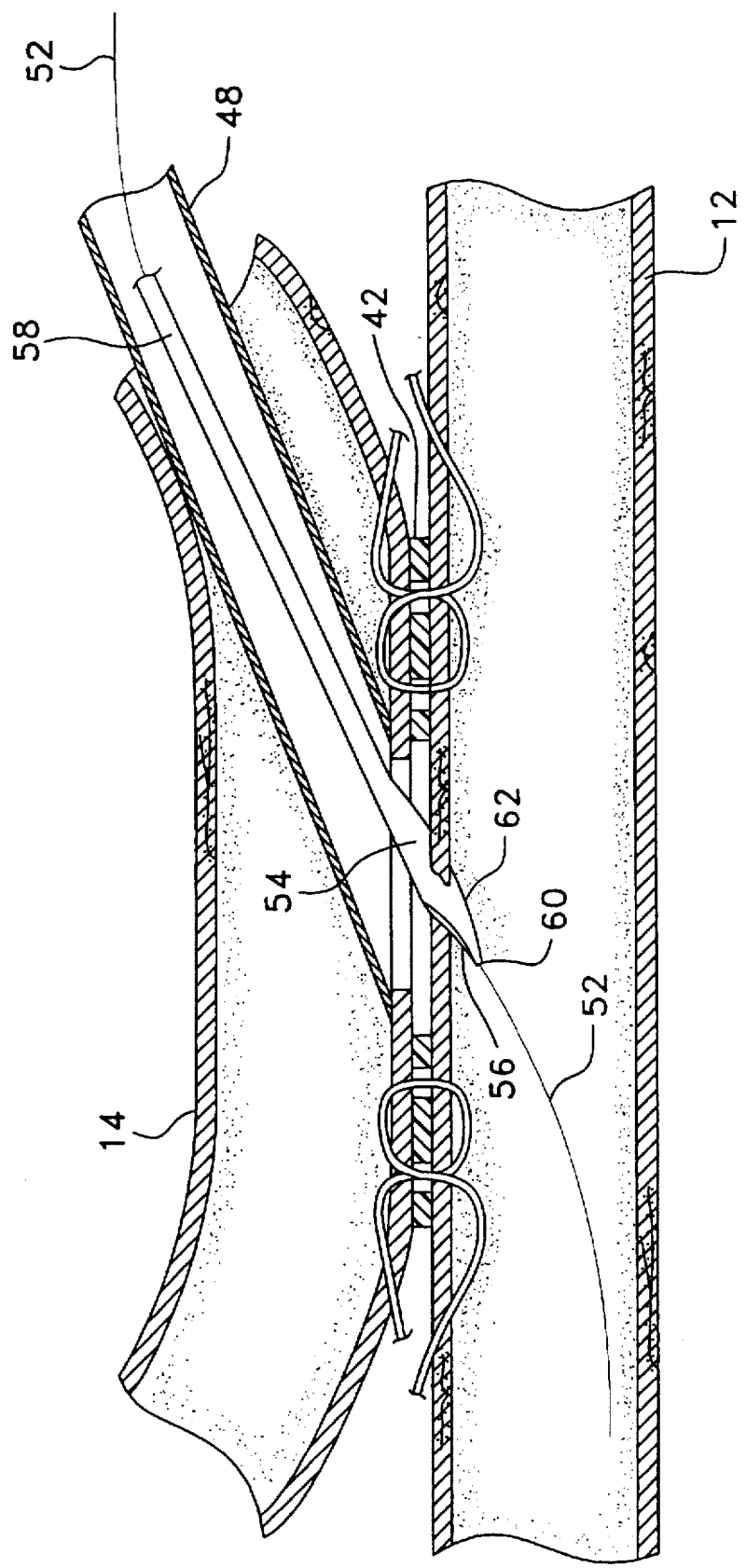
FIG. 16 illustrates cutting of the side wall of the blood vessel according to the present invention.
Figure 17:
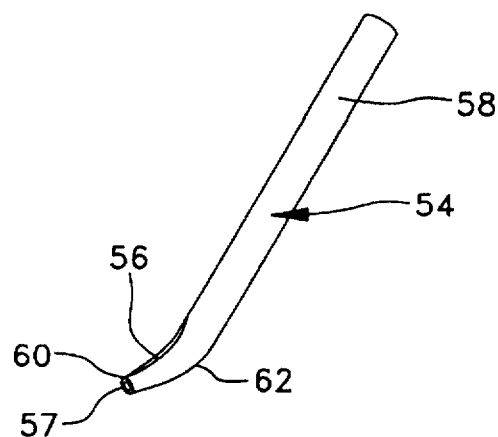
FIG. 17 is a perspective view of one embodiment of the cutting tool according to the present invention.

As shown in FIG. 16, the next step of the procedure involves placing a cutting tool 54 onto the guide wire 52 and directing it into the sleeve 48. The cutting tool 54 (shown in perspective view in FIG. 17) includes a cutting edge 56 and a cutter handle 58. The cutter handle 58 is preferably made from semi-flexible material to permit the physician to control the cutting of the graft and vessel walls. The cutting tool 54 also has a channel 57 formed through it which allows the cutting tool 54 to slide along the guide wire 52. The channel 57 preferably extends through the handle 58 to the tip 60 of the cutting tool 54. The lower portion 62 of the cutting tool 54 is a smooth blunt surface. The overall configuration of the cutting tool is designed to facilitate cutting of the graft and vessel walls while minimizing damage to other areas of the vessel 12. More specifically, the physician uses the cutter handle 58 to push the cutting tool 54 along the guide wire 52 and into the wall of the graft 14. The cutting edge 56 forms a cut or slit in the graft 14 and vessel 12 walls. After the cutting edge 56 passes through the graft and the vessel walls, the guide wire 52 directs the tip 60 and the cutting edge 56 of the cutting tool 54 away from the opposite wall. Accordingly, the only portion of the cutting tool 54 that should contact the opposite wall of the vessel 12 is the lower portion 62 which will not cause any damage to the vessel 12.

Figure 19A:
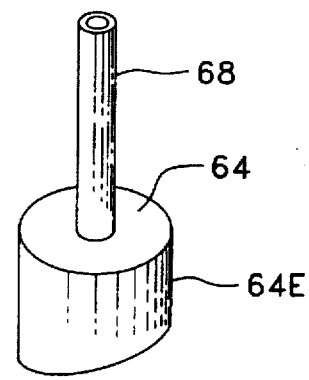
FIGS. 19A and 19B illustrate perspective views of the punch and block as contemplated for use in the present invention.
Figure 19B:
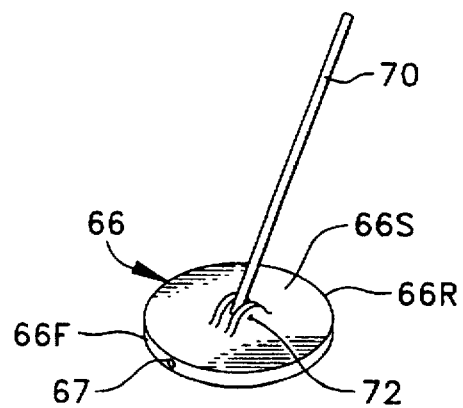
Figure 18:
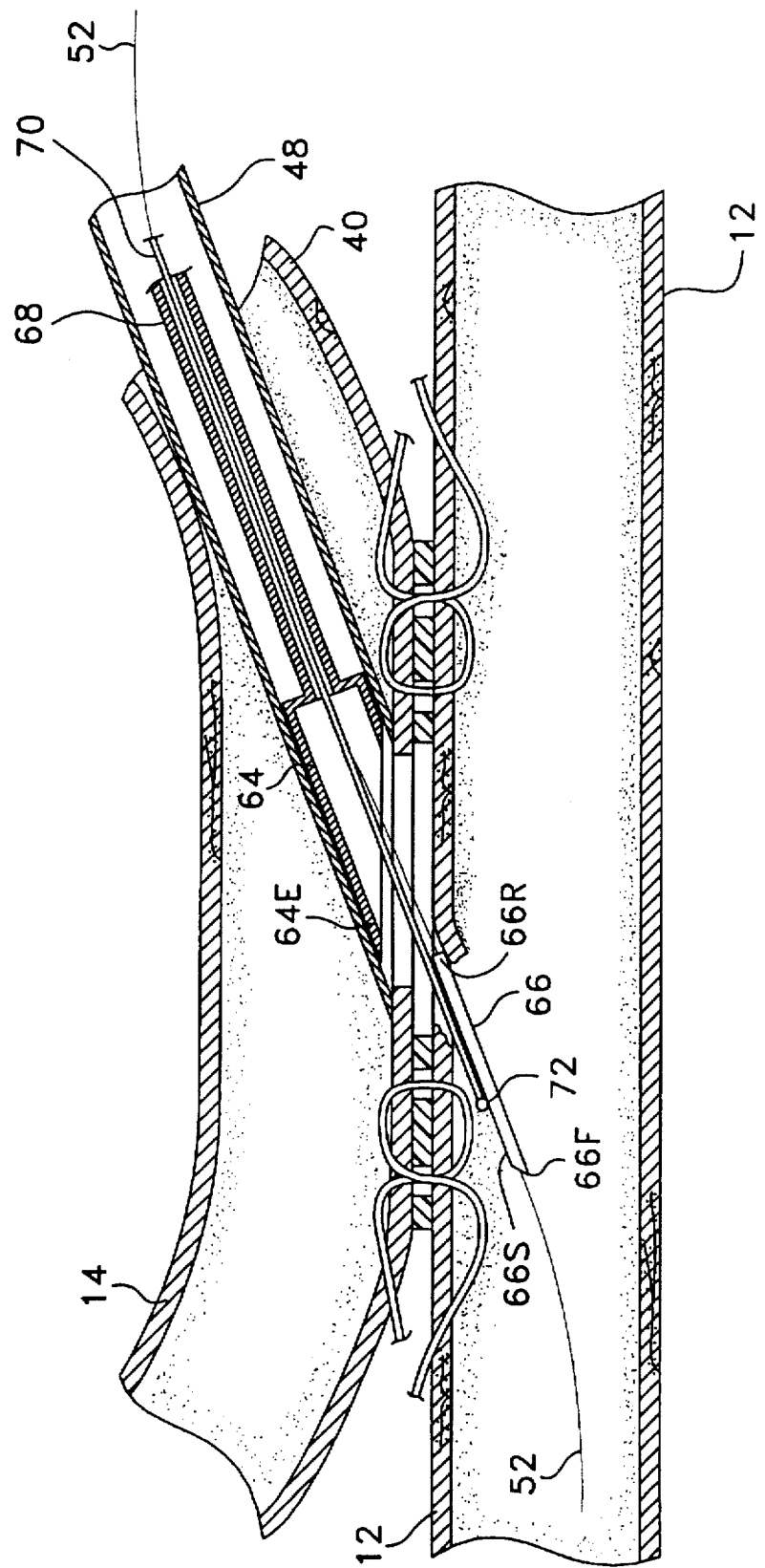
FIG. 18 illustrates positioning of a punch and block during attachment of the graft in a side-to-side grafting according to the present invention.

After the graft 14 and host vessel 12 walls are cut, the cutting tool 54 is removed. A punching device it then inserted into the sleeve 48. A preferred punching device is shown in FIGS. 18, 19A and 19B. This device includes a punch 64 and a block 66. The punch 64 is similar to the punch 30 utilized in the end-to-side grafting embodiment described above except that the punch 64 contacts the graft and vessel walls at an angle less than ninety degrees. As such, the axial length of depending punch side wall $64_W$ of the punch 64 varies around the circumference of the tool so as to provide substantially flush contact with the graft and vessel walls. The punch wall $64_W$ also acts to guide the punch 64 along the sleeve 48 to ensure proper engagement with the graft and vessel walls. The punch 64 has a punch handle 68 similar to the punch handle 36 described previously in the end-to-side grafting embodiment. The physician utilizes the punch handle 68 to assist in positioning the punch within the sleeve 48. The cross-sectional dimensions of the punch 64 is slightly smaller than the cross-sectional dimensions of the sleeve 48 so as to allow the punch to slide within the sleeve 48 while at the same time minimizing the passage of blood.

The block 66, acting in conjunction with the punch 64, defines the resultant opening in the graft and vessel walls through which the blood will flow. One preferred block 66 according to the present invention is shown in FIGS. 18 and 19B and is designed to fit through small hole or cut has been made in the walls of the vessel 12 and graft 14. The block 66 includes a block cutting surface $66_S$ and a block handle 70. The block 66 preferably has a channel 67 formed through at least a portion of it which allows the block 66 to slide along the guide wire 52. The channel preferably extends through the block cutting surface $66_S$ from its rear edge $66_R$ to its front edge $66_F$. Hence, when the block 66 is initially inserted into the angled sleeve 48, the guide wire 52 wire cause the block cutting surface $66_S$ to be substantially parallel to the guide wire 52. This permits the physician to manipulate the block 66 through the cuts in the graft and vessel walls by pushing on the block handle 70. The front edge $66_F$ can be configured to facilitate passage of the block 66 through the cuts in the graft and vessel walls. As shown in FIG. 18, after the block cutting surface $66_S$ enters the lumen of the host vessel 12, the guide wire 52 will direct the front edge $66_F$ of the block 66 away from the opposite vessel wall thereby preventing damage.

The block cutting surface $66_S$ is mounted to the block handle 70 though a pivot (or swivel) attachment 72. The pivot attachment 72 permits the block cutting surface $66_S$ to rotate or pivot about the lower end of the handle 70.

After the block 66 enters the lumen of the host vessel 12, the guide wire 52 is pushed into the host vessel 12 slightly causing the block cutting surface $66_S$ to pivot about the pivot attachment 72. This will result in the block cutting surface $66_S$ being substantially parallel to the interior surface of the host vessel wall.

Figure 20:
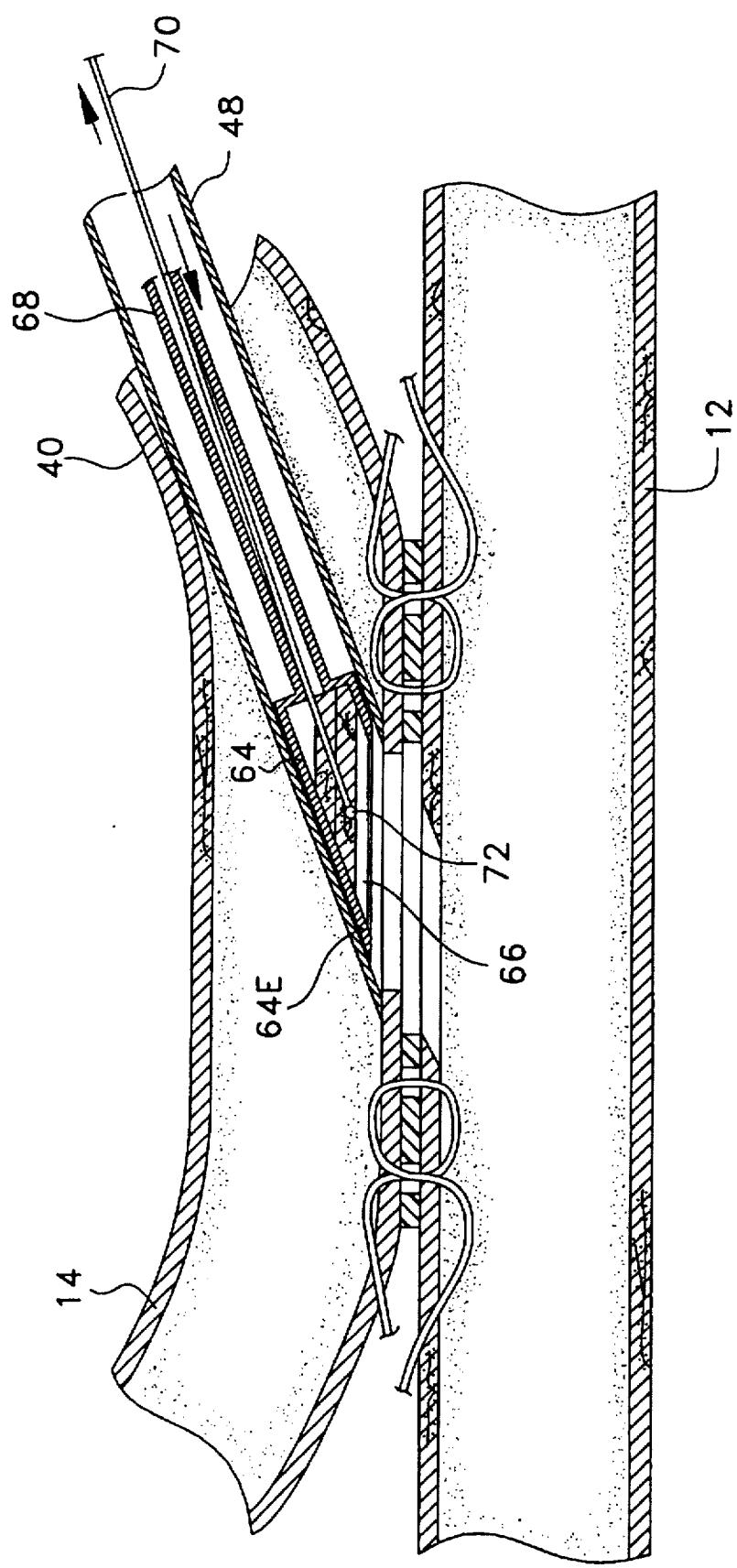
FIG. 20 illustrates removal of a portion of the blood vessel wall during attachment of the graft in a side-to-side grafting according to the present invention.

The punch 64 is then translated toward the vessel wall (shown by the downward arrow in FIG. 20) while, concomitantly, the block 66 is translated toward the punch 64 (shown by the upward arrow in FIG. 20). As a consequence, the vessel and graft walls between the punch 64 and block 66 are sheared off and captured within the punch 64. The capturing of the sheared wall segments within the punch 64 prevents the sheared tissue from entering into the blood stream and causing subsequent damage. Handgrips (not shown) may be incorporated at the distal ends of the punch and block handles 68, 70 to facilitate actuation.

Since the punch 64 and block 66 are punching a hole in the graft 14 and host vessel 12 walls which is at an angle to the normal, the preferred shape of the punch 64 and block 66 (and the resulting hole) is elliptical. However, since the shape of the opening through the vessel and graft walls is not cylindrical, it is preferred that the block 66 be constrained to move in only the axial direction with respect to the punch 64. In order to accomplish this, it is preferred that the punch and block handles 68, 70 have mating non-circular cross-sections. For example, the punch handle 68 would have a square hollow cross-section and the block handle 70 would have a square cross-section that slides within the hollow cross-section of the punch handle 68. Accordingly, the handles will be constrained to move only axially with respect to one another. The punch 64 and block 66 can be made from any suitable material, such as stainless steel or plastic. The diameters of the punch 64 and block 66 will vary depending on the graft lumen diameter and desired bypass inlet size.

As discussed above with respect to the end-to-side grafting embodiment, it is contemplated that the block 66 may be designed to be inflatable from a retracted position to an inflated punching position. The configuration and procedure for using the inflatable block would be similar to the embodiment shown in FIGS. 12A through 12F and described above. Those skilled in the art could readily modify the block embodiment of FIGS. 12A through 12F for use in the side-to-side grafting procedure described above. Alternate embodiments of the punching device can be practiced within the scope of the claims.

After the walls of the graft 14 and vessel 12 have been cut, the blood will begin to flow into the graft 14 from the host vessel 12. The block 66 and punch 64 substantially inhibit passage of the blood out of the terminal end 40 of the graft until a soft clamp is applied to the graft. The terminal end 40 is then sutured or clipped closed after removal of the block 66, punch 64, guide wire 52 and sleeve 48. The clamps at the upstream and downstream ends of the graft are then removed permitting flow of blood through the bypass 10.

In the accompanying figures, the blocks are shown sliding within the depending edges of the punches. It is, however, contemplated that the width of the blocks may be substantially the same as the width of punches.

While the above procedure has been described as being performed without placing the patient on an extracorporeal circuit, it should be readily apparent that a heart-lung machine can be utilized in practicing the invention if desired.

Furthermore, while the above procedure has described the use od an end-to-side attachment at the upstream end of the graft, it is also contemplated that the end-to-side attachment may, instead, be utilized at the downstream end. Alternately, it may be desirable to utilize side-to-side grafting for both ends of the graft.

A dilator can be utilized in the present invention to assist in expanding the end of the graft prior to inserting the sleeves. Also, the graft ends can be cut slightly to facilitate insertion of the sleeves ore permit greater access to the lumen of the graft.

Experimental Results

Several experimental tests of the above procedures were conducted on a series of cows using instruments that were made for the tests. The instruments included three 6.4 mm diameter collars having thicknesses of 0.13 mm, 0.25 mm, and 0.5 mm, respectively. The collars had holes around the perimeter for receiving sutures. The collars were used to attach the graft to the host vessel. A 5 mm diameter disk having a 1.5 mm thickness was also used as the block. A Trefein cylindrical cutter, which is typically utilized for corneal operations, was used as the punch. The Trefein cutter had a diameter of 5 mm and a length of 16 mm. Trefein cutters are sold by Week, Inc., Durham, N.C.

The experiments were carried out in the following manner. An internal mammary artery was harvested from a location within the cow and a small cut was made along one side. A cut was also made in the host vessel. The collar was placed around the cut in the host vessel. Polypropylene sutures with a 6–0 thickness were utilized to attach the collar to the host vessel and the internal mammary artery around the cuts. The steel disk, with a wire attached to it, was inserted into the lumen of the host artery through the cut. The Trefein cutter was inserted into the distal end of the internal mammary artery and positioned adjacent to the host arterial wall. Movement of the Trefein cutter and disk toward one another caused a circular hole to be cut through the wall of the host artery. The Trefein cutter and severed wall section were removed from the internal mammary artery and the distal end of the artery was clipped. Blood recirculation was commenced to ascertain if there was any leakage and to determine whether the blood was flowing properly.

This experimental procedure was performed several times on different cows, each time yielding favorable results for creating an anastomosis.

Although the invention has been described and illustrated with respect to the exemplary embodiments thereof, it should be understood by those skilled in the art that the foregoing and various other changes, omissions and additions may be made therein and thereto, without parting from the spirit and scope of the present invention.

I claim:

1. A punching device for forming an opening within a blood vessel wall during a bypass procedure, the punching device adapted to fit within the lumen of a bypass conduit, the punching device comprising:

a hollow sleeve adapted to be disposed within the lumen of a bypass conduit, the sleeve having an inner width dimension, a punch having a punch wall with a sharp edge portion, the punch wall having an outer width dimension slightly smaller than the inner width dimension of the sleeve so as to permit the punch to slide within the hollow sleeve; and a block having a handle portion attached thereto, the handle portion extending upward through an aperture formed in the punch, the block having a width dimension slightly smaller than the width dimension of the punch;

the sleeve being operative for guiding the punch through the lumen of the bypass conduit and toward a blood vessel wall located adjacent to the bypass conduit;

the punch adapted to act in combination with the block to sever a segment of the blood vessel wall therebetween without damaging the bypass conduit wall within which the punch and block are located.

2. A punching device according to claim 1 wherein the block is configured to fit within an internal diameter of a punch.

3. A punching device according to claim 1 wherein the block further comprises a cutting edge formed on a lower surface of the block and adapted to cut the wall of the blood vessel.

4. A punching device according to claim 3 wherein the cutting edge tapers outward from a tip of the cutting edge to the lower surface of the block.

5. A punching device according to claim 1 wherein the punch includes a hollow punch handle adapted to slidingly receive the block handle therein.

6. A punching device according to claim 5 wherein the block handle and the punch handle have mating cross-sectional shapes.

7. A punching device for forming an opening within a blood vessel wall during a bypass procedure, the punching device adapted to fit within the lumen of a bypass conduit, the punching device comprising:

a punch having a punch wall with a sharp edge portion;

a block having a handle portion attached thereto, the handle portion extending upward through the punch, the punch adapted to act in combination with the block to sever a segment of a blood vessel wall therebetween;

wherein the punch includes a hollow punch handle adapted to slidingly receive the block handle therein, the block handle and the punch handle having mating cross-sectional shapes, and wherein the cross-sectional shapes are non-cylindrical.

8. A punching device according to claim 1 wherein the block handle is attached to the block through a pivotable attachment for permitting the block to pivot about the end of the block handle.

9. A punching device for forming an opening within a blood vessel wall during a bypass procedure, the punching device adapted to fit within the lumen of a bypass conduit, the punching device comprising:

a punch having a punch wall with a sharp edge portion; and a block having a handle portion attached thereto, the handle portion extending upward through the punch, the punch adapted to act in combination with the block to sever a segment of a blood vessel wall therebetween, the block handle being attached to the block through a pivotable attachment for permitting the block to pivot about the end of the block handle wherein the block includes a passage extending through a portion of the block, the passage adapted to receive a guide wire for guiding the block during insertion into the blood vessel.

10. A punching device for forming an opening within a blood vessel wall during a bypass procedure, the punching device adapted to fit within the lumen of a bypass conduit, the punching device comprising:

a punch having a punch wall with a sharp edge portion; and a block having a handle portion attached thereto, the handle portion extending upward through the punch, the punch adapted to act in combination with the block to sever a segment of a blood vessel wall therebetween, wherein the block handle has a channel formed in it, the punching device further comprising a cutter having a cutting edge attached to a cutter handle, the cutter handle extending up within the channel formed within the block handle.

11. A punching device according to claim 10 further comprising biasing means disposed between the cutter handle and the block handle so as to permit biasing therebetween, and wherein the block includes a recess formed on its lower surface and adapted to receive the cutting edge of the cutter therein.

12. A punching device according to claim 1 wherein the block is expandable from a collapsed position to an expanded position, the collapsed position being adapted to permit the block to be inserted into the lumen of the vessel.

13. A punching device for forming an opening within a blood vessel wall during a bypass procedure, the punching device adapted to fit within the lumen of a bypass conduit, the punching device comprising:

a punch having a punch wall with a sharp edge portion; and block having a handle portion attached thereto, the handle portion extending upward through the punch, the punch adapted to act in combination with the block to sever a segment of a blood vessel wall therebetween, the block being expandable from a collapsed position to an expanded position, the collapsed position being adapted to permit the block to be inserted into the lumen of the vessel, and wherein the block is in fluidic communication with a channel formed in the block handle, the channel adapted to receive a fluid medium for expanding the block from its collapsed position to its expanded position.

14. A punching device according to claim 1 wherein the sharp edge portion is adapted to contact the blood vessel wall substantially flush.

15. A punching device for forming an opening within a blood vessel wall during a bypass procedure, the punching device adapted to fit within the lumen of a bypass conduit, the punching device comprising:

a punch having a punch wall with a sharp edge portion, the sharp edge portion adapted to contact the blood vessel wall substantially flush; wherein the punch wall is at an angle to the blood vessel wall which is less than perpendicular when the sharp edge portion is substantially flush with the blood vessel wall; and a block having a handle portion attached thereto, the handle portion extending upward through the punch, the punch adapted to act in combination with the block to sever a segment of a blood vessel wall therebetween.

* * * * *